US 9,428,073 B2

(12) United States Patent
Baughman et al.

(10) Patent No.: US 9,428,073 B2
(45) Date of Patent: Aug. 30, 2016

(54) SYSTEM AND METHOD OF MONITORING A PERFORMANCE LEVEL OF A BATTERY

(71) Applicant: GM GLOBAL TECHNOLOGY OPERATIONS LLC, Detroit, MI (US)

(72) Inventors: Andrew C. Baughman, Northville, MI (US); Daniel P. Grenn, Highland, MI (US); Andrew M. Zettel, Port Moody (CA)

(73) Assignee: GM Global Technology Operations LLC, Detroit, MI (US)

( * ) Notice: Subject to any disclaimer, the term of this patent is extended or adjusted under 35 U.S.C. 154(b) by 168 days.

(21) Appl. No.: 14/186,750

(22) Filed: Feb. 21, 2014

(65) Prior Publication Data

US 2015/0239364 A1 Aug. 27, 2015

(51) Int. Cl.
*H02J 7/00* (2006.01)
*B60L 3/04* (2006.01)
(Continued)

(52) U.S. Cl.
CPC .......... *B60L 11/1861* (2013.01); *B60L 3/0046* (2013.01); *B60L 3/04* (2013.01); *B60L 3/12* (2013.01); *B60L 11/1864* (2013.01); *B60L 15/20* (2013.01); *G07C 5/0808* (2013.01); *G07C 5/0841* (2013.01); *B60L 2210/10* (2013.01); *B60L 2240/12* (2013.01); *B60L 2240/423* (2013.01); *B60L 2240/443* (2013.01); *B60L 2240/545* (2013.01); *B60L 2240/547* (2013.01); *B60L 2240/549* (2013.01); *B60L 2260/26* (2013.01); *G01N 27/416* (2013.01); *G08B 21/00* (2013.01); *H02J 7/00* (2013.01); *Y02T 10/705* (2013.01); *Y02T 10/7044* (2013.01); *Y02T 10/7055* (2013.01); *Y02T 10/7077* (2013.01); *Y02T 10/7283* (2013.01)

(58) Field of Classification Search
CPC ................ H02J 7/00; H02J 7/04; H02J 7/16; G01N 27/416; G08B 21/00; Y02T 10/7044; Y02T 10/705; Y02T 10/7055; Y02T 10/7077; Y02T 10/7283; B60L 11/1861; B60L 3/12; G07C 5/0808; G07C 5/0841
USPC ........ 320/132, 134, 136, 152, 162; 324/432; 340/636.12, 636.13, 636.18; 307/150
See application file for complete search history.

(56) References Cited

U.S. PATENT DOCUMENTS 5,644,212 A * 7/1997 Takahashi ........... B60L 11/1809
320/134
9,156,356 B2 * 10/2015 Rini ...................... H02J 7/0031
(Continued)

FOREIGN PATENT DOCUMENTS

JP 2000019232 A * 1/2000 ................ H02J 7/00

OTHER PUBLICATIONS

Tatsuhiko et al., Mahcine English Translation of Japanese Document No. JP-20014-072992, published Apr. 21, 2014, mahcine translated by JPO, machine translated on Sep. 8, 2015, 24 pages.*

*Primary Examiner* — Phallaka Kik
(74) *Attorney, Agent, or Firm* — Quinn Law Group, PLLC

(57) ABSTRACT

A method of monitoring a performance level of a battery of a vehicle having an electronic control unit (ECU) includes enabling a charging diagnostic module (CDM) and determining, with the CDM, a charging status of the battery. The method also includes enabling a discharging diagnostic module (DDM) and determining, with the DDM, a discharging status of the battery. The charging status and the discharging status are recorded in a memory location of the ECU.

20 Claims, 2 Drawing Sheets

(51) Int. Cl.
*B60L 11/00* (2006.01)
*B60L 15/20* (2006.01)
*G01N 27/416* (2006.01)
*G07C 5/00* (2006.01)
*B60L 11/18* (2006.01)
*B60L 3/12* (2006.01)
*G07C 5/08* (2006.01)
*B60L 3/00* (2006.01)
*G08B 21/00* (2006.01)

(56) References Cited

U.S. PATENT DOCUMENTS

| | | | | |
|---|---|---|---|---|
| 9,246,337 | B2* | 1/2016 | Iwasawa | G01R 31/3679 |
| 9,263,901 | B2* | 2/2016 | Boggs | B60L 3/00 |
| 9,281,517 | B2* | 3/2016 | Matsushita | H01M 4/366 |
| 9,306,403 | B2* | 4/2016 | Fink | H02J 7/0013 |
| 2003/0029654 | A1* | 2/2003 | Shimane | B60K 6/28 180/65.29 |
| 2010/0123465 | A1* | 5/2010 | Owens | G01R 31/026 324/503 |
| 2011/0078092 | A1* | 3/2011 | Kim | B60L 11/1824 705/412 |
| 2012/0043939 | A1* | 2/2012 | Ju | H02J 7/0072 320/129 |
| 2012/0169270 | A1* | 7/2012 | Cho | H01M 10/441 320/101 |
| 2012/0256569 | A1* | 10/2012 | Kawahara | H01M 10/486 318/139 |
| 2013/0069584 | A1* | 3/2013 | Nagakura | H02J 7/0086 320/107 |
| 2013/0257381 | A1* | 10/2013 | Diamond | B60L 11/1861 320/134 |
| 2014/0058598 | A1* | 2/2014 | Matsui | H01M 4/131 701/22 |
| 2014/0062398 | A1* | 3/2014 | Satake | B60L 11/1809 320/109 |
| 2014/0141303 | A1* | 5/2014 | Matsushita | H01M 4/366 429/94 |
| 2014/0285936 | A1* | 9/2014 | Garbacik | B60L 11/1866 361/88 |

* cited by examiner

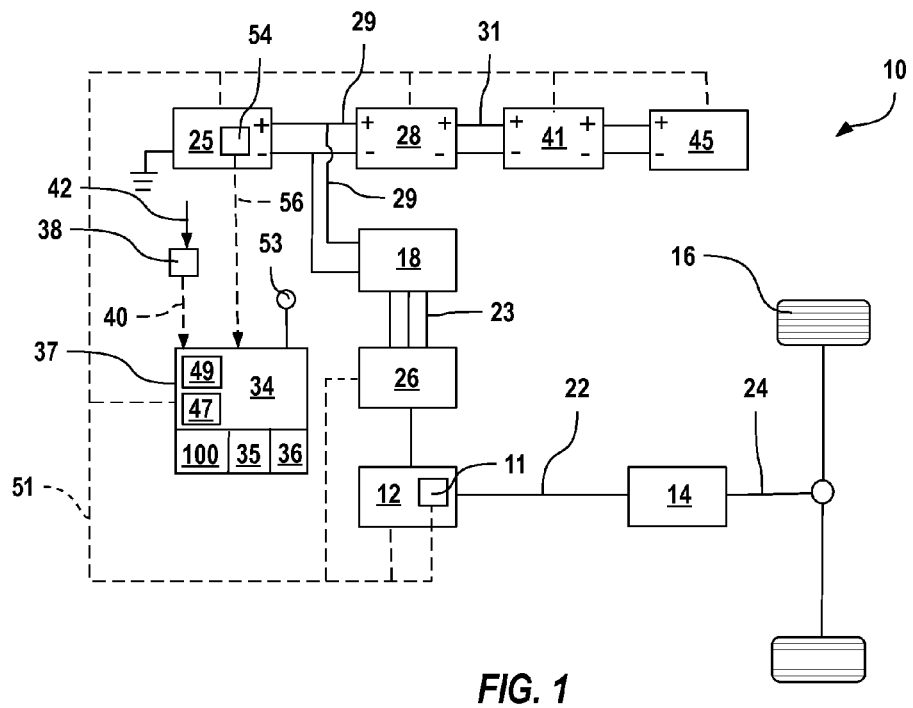
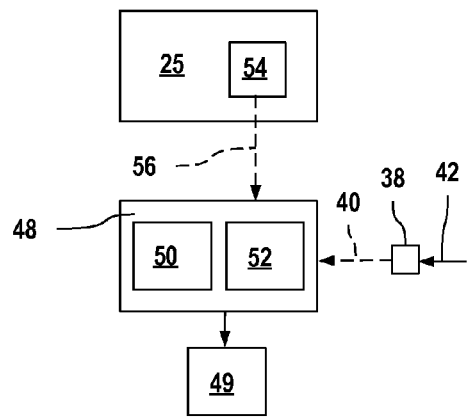
FIG. 2
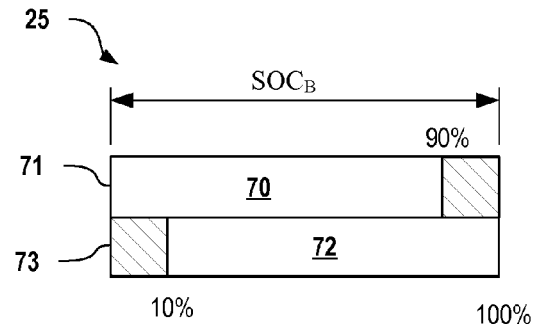
FIG. 3

SYSTEM AND METHOD OF MONITORING A PERFORMANCE LEVEL OF A BATTERY

TECHNICAL FIELD

The present disclosure is related to a system and method of monitoring a performance level of a battery.

BACKGROUND

Motorized vehicles include a powertrain operable to propel the vehicle and power the onboard vehicle electronics. The powertrain, or drivetrain, generally includes an engine that powers the final drive system through a multi-speed power transmission. Many vehicles are powered by a reciprocating piston type internal combustion engine (ICE).

Hybrid vehicles utilize multiple alternative power sources to propel the vehicle, minimizing reliance on the engine for power. A hybrid electric vehicle (HEV), for example, incorporates both electric energy and chemical energy, and converts the same into mechanical power to propel the vehicle and power the vehicle systems. The HEV generally employs one or more electric machines (motor/generators) that operate individually or in concert with the internal combustion engine to propel the vehicle.

The electric machines convert kinetic energy into electric energy which may be stored in an energy storage device. The electric energy from the energy storage device may then be converted back into kinetic energy for propulsion of the vehicle. Electric vehicles also include one or more electric machines and energy storage devices used to propel the vehicle. Conventional vehicles may include an electric machine to convert kinetic energy of the engine into electric energy which is stored in a starting, lighting, and ignition (SLI) battery.

SUMMARY

One possible aspect of the disclosure provides a method of monitoring a performance level of a battery of a vehicle having an electronic control unit (ECU). The method includes enabling a charging diagnostic module (CDM) and determining, with the CDM, a charging status of the battery. The method also includes enabling a discharging diagnostic module (DDM) and determining, with the DDM, a discharging status of the battery. The charging status and the discharging status are recorded in a memory location of the ECU.

In another aspect of the disclosure, a vehicle includes a battery and a controller in communication with the battery. The controller is configured to enable a charging diagnostic module (CDM) and determine, with the CDM, a charging status of the battery. The controller is also configured to enable a discharging diagnostic module (DDM) and determine, with the DDM, a discharging status of the battery. The controller also records the charging status and the discharging status in a memory location of the ECU.

The above features and advantages and other features and advantages of the present teachings are readily apparent from the following detailed description of the best modes for carrying out the present teachings when taken in connection with the accompanying drawings.

BRIEF DESCRIPTION OF THE DRAWINGS

FIG. 1 is a schematic illustration of an example vehicle having a battery and a controller which monitors the performance level of the battery.

FIG. 2 is a schematic logic flow diagram for the controller usable with the vehicle shown in FIG. 1.

FIG. 3 is a schematic diagrammatic illustration of a charging side and a discharging side of the battery.

DETAILED DESCRIPTION

Figure 4:
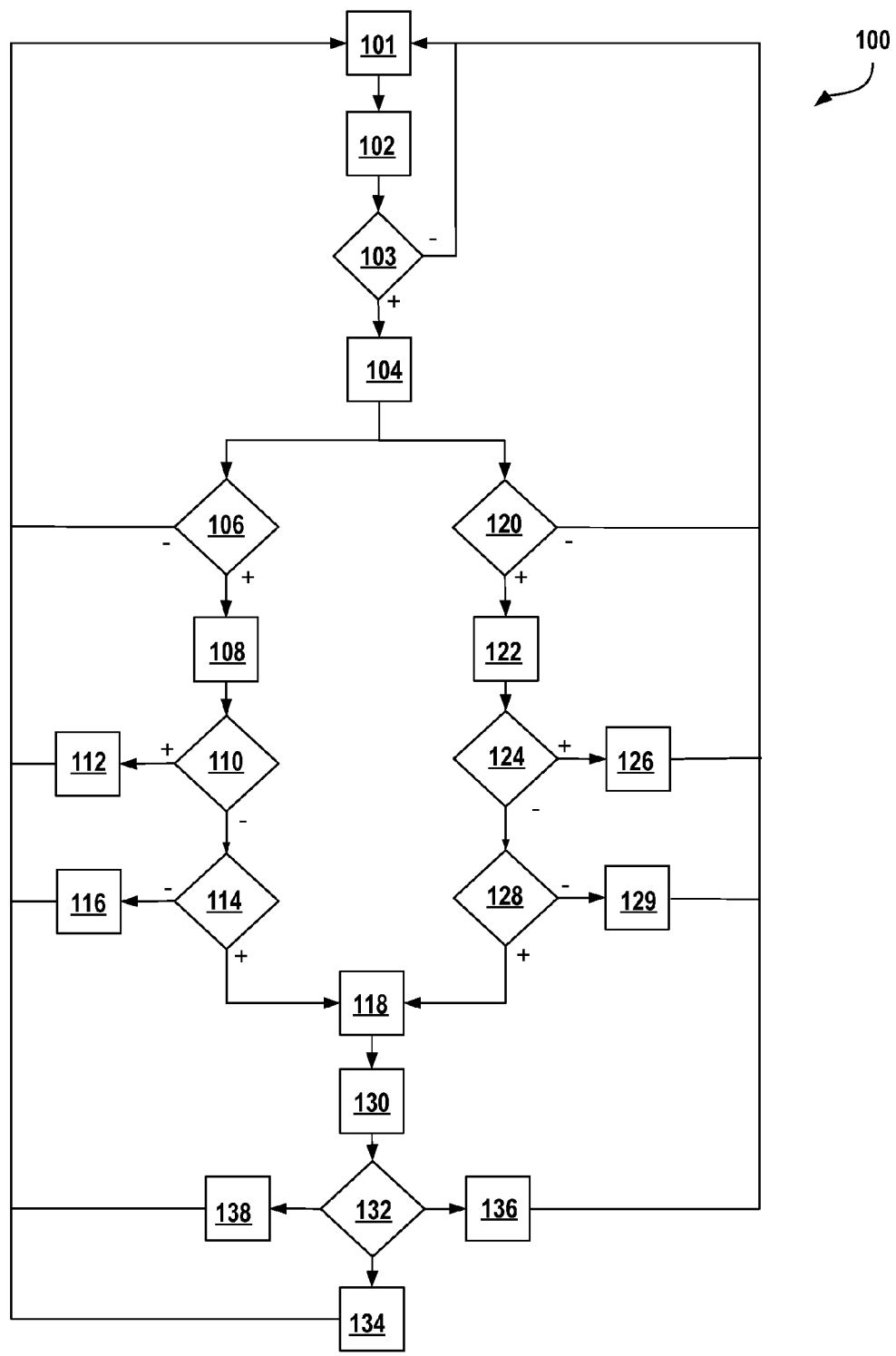
FIG. 4 is a flow chart describing a method for monitoring the performance level of the battery of the vehicle shown in FIG. 1.

Referring to the drawings wherein like reference numbers correspond to like or similar components throughout the several figures, and beginning with FIG. 1, a vehicle, such as a hybrid electric vehicle (HEV) 10, includes an internal combustion engine 12 having a starter motor 11 operable for starting the engine 12 during an initial start-up of the HEV 10. The HEV 10 also includes a transmission 14, having an input member 22. The transmission 14 is configured to be capable of transmitting propulsive torque to a set of road wheels 16, via an output member 24, operatively connected to the transmission 14.

The HEV 10 may include a high-voltage electric motor/generator unit (MGU) 26 that is operatively connected to the engine 12. The MGU 26 may be configured to selectively crank and start the engine 12. In some embodiments, the starter motor 11 may be used for the same purpose. The MGU 26 may be configured as a multi-phase electric machine having a relatively high voltage of approximately 60 volts to 300 volts or more, depending on the design. The MGU 26 is also electrically connected to a rechargeable energy storage system (RESS) 25 via a high-voltage DC bus or connection 29, a power inverter module (PIM) 18, and an alternating current (AC) bus 23. The RESS 25 may be a multi-cell lithium ion or suitable battery pack in a possible embodiment. Further, the RESS 25 may be configured as a high-voltage battery having a plurality of cells and configured to store and provide electrical energy to one or more electrical components in the HEV 10. As such, the RESS 25 may be configured to selectively propel the HEV 10 by supplying electrical power to the MGU 26, which in turn drives the transmission 14, and ultimately the wheels 16 in an electric mode. The RESS 25 may be recharged via the MGU 26 when the MGU 26 is operating in its capacity as a generator, for example during a regenerative braking event, as known to those of skill in the art.

As discussed in greater detail below, the RESS 25 may include one or more sensors 54. The RESS 25 may have one or more parameter values that are associated with a performance level of the RESS 25. The performance level may include a quantity representing a condition of the RESS 25 relative to ideal operating conditions of the RESS 25. Thus, the performance level may be used to determine the remaining lifespan of the RESS 25. The parameter values may be quantities that are used to estimate or derive the performance level. Another quantity, called the state of charge (SOC), may indicate the residual (e.g., remaining) capacity of the RESS 25 relative to a reserve capacity of the RESS 25. Thus, the state of charge is an indication of how much electrical energy may be provided before the RESS 25 needs to be recharged.

The sensor 54 may include any device configured to measure a terminal voltage, an accumulated charge, and temperatures of the RESS 25 and generate one or more signals representing those measured characteristics. While only one sensor 54 is illustrated, the HEV 10 may include any number of sensors 54. For instance, one sensor may be used to measure a voltage, another sensor may be used to measure an accumulated charge, and different sensor may be used to measure the temperature.

To measure the voltage, the sensor 54 may include a digital or analog voltmeter configured to measure a difference in electrical potential across terminals of the RESS 25. Alternatively, the sensor 54 may be configured to estimate or derive the voltage across the terminals based on factors such as the current output of the RESS 25, the temperature of the RESS 25, and the resistance of components within the RESS 25. The voltmeter may be configured to generate and output a signal representative of the electrical potential across the terminals (e.g., the terminal voltage). To measure the accumulated charge, the sensor 54 may include any device configured to measure electrical current (e.g., direct current) and generate a signal representative of the magnitude of the current measured. The accumulated charge may be derived from the measured terminal current. To measure the temperature of the RESS 25, the sensor 54 may include any device configured to measure a quantity of heat at one or more locations of the RESS 25, including the ambient air surrounding the RESS 25, and generate one or more signals that represent the highest, lowest, average, and/or median temperature measured.

The HEV 10 may also include an auxiliary power module or APM 28, which is electrically connected to the RESS 25 via a high-voltage bus 29, and to a low-voltage or auxiliary battery (AUX) 41 via a low-voltage bus 31. The APM 28 may be configured as a DC-DC converter adapted to convert a supply of DC power from a high-voltage level to a low-voltage level, and vice versa, as determined by an electronic control unit (ECU) 37. More specifically, the APM 28 is operable for converting a relatively high voltage from the ESS 25 to a lower voltage level suitable for charging the auxiliary battery 41, and for supplying the HEV 10 with low-voltage power, as required. The auxiliary battery 41 may be a relatively low-level device, such as a 12-volt battery, suitable for powering one or more auxiliary systems or accessories 45 aboard the HEV 10.

Still referring to FIG. 1, the ECU 37 is operatively connected to or otherwise in communication with each of the engine 12, the starter motor 11, the MGU 26, the RESS 25, the APM 28, and the auxiliary battery 41 via a control channel 51, e.g., a hard wired or wireless control link or path suitable for transmitting and receiving the necessary electrical control signals for proper power flow coordination within the HEV 10. The ECU 37 includes a microprocessor unit that receives and processes various vehicle operating values including an APM voltage output and an APM current output. The ECU 37 may be configured as a distributed or a central control module having such control modules and capabilities as might be necessary to execute all required power flow control functionality aboard the HEV 10 in the desired manner.

In response to receiving an input 42 from operator (driver), the HEV 10 is also configured with an ignition system 38 configured to transmit an ignition signal 40 to the ECU 37 to, in turn, initiate a "RUN/CRANK" event and thus start the engine 12. The input 42 may be turning a key in the ignition. Some configurations of the HEV 10 may not include a traditional (key-based) ignition, and may be operational whenever the operator of the HEV 10 is within proximity of the HEV 10. For example, the ignition system 38 may be configured to transmit the signal 40 to the HEV 10 and may be operational whenever a key fob or remote security device (not shown) is inside of the vehicle or whenever a start button (not shown) is pushed.

Additionally, the ECU 37 includes a controller 34. The physical hardware embodying the controller 34 may include one or more digital computers having a processor 35 and a memory 36, e.g., a read only memory (ROM), random access memory (RAM), electrically-programmable read only memory (EPROM), high speed clock, analog to digital (A/D) and digital to analog (D/A) circuitry, and input/output circuitry and devices (I/O) including one or more transceivers 47 for receiving and transmitting any required signals in the executing of method 100, as well as appropriate signal conditioning and buffer circuitry. Any computer-code resident in the controller 34 or accessible thereby, including the algorithm 100, can be stored in the memory 36 and executed via the processor(s) 35 to provide the functionality set forth below.

The controller 34 of FIG. 1 may be configured as a single or, as shown in FIG. 2 a distributed control device. The controller 34 is electrically connected to or otherwise in hard-wired or wireless communication with each of the engine 12, the MGU 26, the RESS 25, the APM 28, and the PIM 18 via suitable control channels 51, e.g., a controller area network (CAN) or serial bus, including for instance any required transfer conductors, whether hard-wired or wireless, sufficient for transmitting and receiving the necessary electrical control signals for proper power flow control and coordination aboard the HEV 10.

With continued reference to FIG. 1, the controller 34 may be configured to estimate or derive one or more of the parameter values associated with the state of health of the RESS 25, as well as determine the state of charge of the RESS 25. In one possible implementation, the controller 34 may be configured to determine when the RESS 25 has reached a minimum performance level and then record the status of the performance level of the RESS 25 in a data manager 49. More specifically, in this implementation, the status recorded in the data manager 49 may reflect that the RESS 25 has reached an end of its usable life and/or requires maintenance. The data manager 49 may be resident within the ECU 37 or may be disposed in any other desired location. The data manager 49 may, in turn, be configured to illuminate a display indicator 53 and/or set a "fault".

Referring to FIG. 2, in a particular configuration, the controller 34 of FIG. 1 may include multiple control modules, each having corresponding hardware and software which together perform corresponding functions, possibly executed at faster or slower process loop speeds relative to the other control modules. For example, a battery diagnostic module (BDM) 48 may include, or be in communication with, a charging diagnostic module (CDM) 50 and a discharging diagnostic module (DDM) 52. While omitted from FIG. 2 for illustrative clarity, each control module 48, 50, 52 may include one or more of the processors 35, memory 36, and transceivers 47, as shown in FIG. 1.

The CDM 50 is configured to function as a monitoring system that monitors a charging capability 70 of the RESS 25. Likewise, the DDM 52 is configured to function as a separate monitoring system that monitors a discharging capability 72 of the RESS 25. The CDM 50 and the DDM 52 function simultaneously. As set forth in more detail below, each monitor 50, 52 will "pass" if its monitored input is greater than or equal to a calibrated fault threshold and each monitor 50, 52 will fail if the input is less than a calibrated fault threshold. If either monitor 50 or 52 fails during a drive cycle of the HEV 10, the BDM 48 also fails. However, if both monitors 50 and 52 pass during the drive cycle, the BDM 48 also passes. Therefore, monitoring both the charging and discharging power capabilities of the RESS 26 allows the entire band of the state of charge of the battery of the RESS 25 to have at least one diagnostic monitor 50, 52 enabled.

With continued reference to FIG. 2, the controller 34 may continuously receive a signal 40 from the ignition system 38 and one or signals 56 from the RESS 25. The signals 56 from the RESS 25 may be related to the voltage, state of charge, temperature, current, and the like. The controller 34 may store these signals 38, 56 in the memory 36 as values to be used by the modules 48, 50, 52, as set forth in more detail below.

The BDM 48 performs a diagnostic that continuously monitors the performance of the RESS 25 to determine whether or not the RESS 25 has reached the minimum performance level. The BDM 48 senses, via the signal inputs 40, 56, when a pre-defined minimum performance level is not met by the RESS 25. The BDM 48 is capable of simultaneously monitoring the charging power limit, via the CDM 50, and the discharging power limit, via the DDM 52, thus ensuring that at least one of the modules 50, 52 is active at any particular state of charge of the RESS 25. When the state of charge is too high, the charging capability estimate will be inaccurate, but the discharging capability estimate will be accurate. Likewise, when the state of charge is too low, the discharging capability estimate will be inaccurate, but the charging capability estimate will be accurate. Said differently, when the state of charge is high enough or low enough to cause inaccuracy in one capability estimation, i.e., charging or discharging, the estimation of the other of the charging and discharging will still be accurate. The diagnostic of the BDM 48 is configured to fail if the calculated battery power falls below acceptable power levels and the diagnostic of the BDM 48 is configured to pass if a reasonable drive cycle of the HEV 10 is completed without a fault. If the diagnostic of the BDM 48 fails, in order to re-pass the diagnostic of the BDM 48, additional conditions may be added to the diagnostic in order to attempt to duplicate the conditions of the original fault mode and verify that indeed the fault mode is no longer present during operation of the HEV 10.

With continued reference to FIG. 2, the BDM 48 simultaneously communicates with the CDM 50 and the DDM 52, where the CDM 50 and the DDM 52 each monitor separate fault conditions of the RESS 25. With reference to FIG. 3, the CDM 50 monitors, in part, a charging capability 70 of a charging side 71 of the RESS 25, the DDM 52 monitors a discharging capability 72 of a discharging side 73 of the RESS 25. More specifically, the CDM 50 observes and monitors a calculated battery power capability for accepting charging power by the charging side 71 and the DDM 52 observes and monitors a calculated battery power capability for providing discharging power by the discharging side 73. By way of a non-limiting example, with continued reference to FIG. 3, the RESS 25 may be capable of estimating a charging power capability 70 from the charging side 71 when a state of charge on the charging side 71 is no greater than a 90% state of charge. Likewise, the RESS 25 may be capable of estimating a discharging power capability 72 by the discharging side 73 when a state of charge of the discharging side 73 is no less than a 10% state of charge. As will be explained in more detail below, each module 50, 52 has its own enabling conditions with respect to a state of charge, temperature, current, power capability, recent battery usage, and the like. The state of charge of enablement regions for charging and discharging (see FIG. 3), while unique, have the capability to overlap, thus extending the power capability diagnosis to cover all possible state of charges of the RESS 25.

With respect to the operation of the controller 34 in execution of the method 100, the method 100 may begin at step 101, wherein the controller 34 receives signals 56 from the RESS 25. Once the signals 56 are received from the RESS 25, the method 100 proceeds to step 102.

At step 102, the received signals 56 are stored in the memory 36 as values. The values may be associated with a voltage (V), state of charge ($SOC_B$), minimum battery temperature ($T_{BMIN}$), maximum battery temperature ($T_{MAX}$), current (I), and the like. The voltage (V) is the sensor voltage sensed across all battery cells within the RESS 25. The state of charge ($SOC_B$) indicates a percentage of remaining electric charge (i.e., Amphours) in the RESS 25 with respect to the total possible stored charge, without respect to a normal operating range or usage window. Temperature affects battery impedance (i.e., higher temperature means lower impedance and lower temperature means higher impedance), and hence, the power capability of the RESS 25. The maximum temperature ($T_{MAX}$) and the minimum temperature ($T_{MIN}$) are used as a mechanism to ensure that the temperature spread across cells of the RESS 25 is not so large that the impedance range causes the RESS 25 to not be capable of accurate diagnosis. To keep the cell voltages within the control boundary, a battery control system can only allocate as much power as the least capable cells can take; with respect to temperature, the coldest cells are the least capable. Once the values are stored in the memory 36, the method 100 proceeds to step 103.

At step 103, the controller 34 determines whether the ignition signal 40 is being received by the ECU 37. If the ignition signal 40 is not being received by the ECU 37, the method 100 returns to step 101, where the method 100 is repeated.

If the ignition signal 40 is being received by the ECU 37, the method 100 proceeds to step 104.

At step 104, the controller 34 retrieves the values from the memory 36. Next, the method simultaneously proceeds to steps 106 and 120.

At step 106, a determination is made as to whether the CDM 50 should be enabled, as a function of the values of the RESS 25 and the ignition signal. More specifically, the controller 34 determines that the CDM 50 should be enabled only when certain conditions are met. These conditions may include, but should not be limited to, determining that the voltage ($V_B$), state of charge ($SOC_B$), minimum battery temperature ($T_{BMIN}$), maximum battery temperature ($T_{BMAX}$), current ($I_B$), and a calculated charging power limit are all available and also determining that the ignition signal 40 is being received. The calculated charging power level provides the ability to choose which of the high voltage battery charging power limits are observed in the CDM 50. The conditions may also require the voltage ($V_B$), state of charge ($SOC_B$), minimum battery temperature ($T_{BMIN}$), maximum battery temperature ($T_{BMAX}$), current ($I_B$), and a calculated charging power limit are not fault active at the same time the ignition signal 40 is consecutively being received 40.

Further conditions to meet the enablement conditions for the CDM 50 may include that the state of charge ($SOC_B$) is greater than or equal to a minimum enabled state of charge ($SOC_{EMIN}$), based on a charging calibration; the state of charge ($SOC_B$) is less than or equal to a maximum enabled state of charge ($SOC_{EMAX}$), based on the charging calibration; the maximum temperature ($T_{BMAX}$) is less than or equal to a calibrated maximum enabled temperature ($T_{EMAX}$); the minimum temperature ($T_{BMIN}$) is greater than or equal to a calibrated minimum enabled temperature ($T_{EMIN}$); and a difference between the maximum temperature ($T_{BMAX}$) and minimum temperature ($T_{BMIN}$) is less than or equal to a calibrated maximum delta temperature ($T_{\Delta MAX}$). Other conditions may be required in order to enable the CDM 50. The minimum enabled state of charge ($SOC_{EMIN}$) is the ability to choose the lowest value for the state of charge ($SOC_B$) for which the CDM 50 will still be enabled. The maximum enabled state of charge ($SOC_{EMAX}$) is the ability to choose the highest value for the state of charge ($SOC_B$) for which the CDM 50 will still be enabled. The maximum enabled temperature ($T_{EMAX}$) is the ability to choose the highest value for the maximum temperature ($T_{BMAX}$) for which the CDM 50 will still be enabled. Likewise, the minimum enabled temperature ($T_{EMIN}$) is the ability to choose the lowest value for the minimum temperature ($T_{BMIN}$) for which the CDM 50 will still be enabled. The calibrated maximum delta temperature ($T_{\Delta MAX}$) is the ability to choose the largest difference between the maximum and minimum high voltage battery temperature ($T_{BMAX}$), ($T_{BMIN}$) for which the CDM 50 will still be enabled.

If the determination is made at step 106 that the CDM 50 should not be enabled, the method returns to step 101, where the method 100 repeats. If, however, the determination is made at step 106 that the CDM 50 should be enabled, the method proceeds to step 108, where the CDM 50 is enabled.

Next, the method proceeds from step 108 to step 110. At step 110 a determination is made as to whether fault conditions are met, based on a charging calibrated threshold for greater than a charging fault count limit. The charging fault count limit may provide the ability to choose, during calibration, how many samples of consecutive instantaneously failed data in a sample period it should take to produce a fault determination for the CDM 50. At step 110, fault conditions are met if, based on the charging calibrated threshold, the calculated charging power limit indicates lesser power capability than an end of life power threshold, based on the charging calibrated threshold, for the relevant battery state of charge ($SOC_B$) and the battery minimum temperature ($T_{BMIN}$). The end of life power threshold provides the ability to choose the charging power threshold for fault for the CDM 50.

If the determination is made at step 110 that the fault conditions are met, the method proceeds to step 112. At step 112, the status of the fault conditions not being met is recorded in a memory location within the data manager 49 and the method 100 returns to step 102, where the algorithm repeats. If, however, the determination is made at step 110 that the fault conditions are not met, the method proceeds to step 114.

At step 114, a determination is made as to whether pass conditions are met for the CDM 50. More specifically, the pass conditions are met if all of the following have occurred while the ignition signal 40 (i.e., RUN/CRANK) was consecutively True: (1) a product of the voltage ($V_B$) and the current ($I_B$) are of greater power in a charging direction than a minimum pass power threshold, based on a charging calibration, as a function of the relevant battery state of charge ($SOC_B$) and the minimum battery temperature ($T_{BMIN}$), for greater than a minimum pass power duration, based on a charging calibrated number of consecutive diagnostic executions; and (2) either of the following occur: (a) a first fault power level, for charging, is equal to a first fault power initialization calibration; or (b) all of the following are true for greater than a minimum re-pass condition met duration, for charging, based on a calibrated consecutive number of diagnostic executions: (i) the first fault power level, for charging, is not equal to the first fault power initialization calibration; (ii) the absolute value of a difference between the battery state of charge ($SOC_B$) and a first fault state of charge ($SOC_{FF}$), during charging, is less than a state of charge re-pass hysteresis calibration ($SOC_{RPC}$); and (iii) the absolute value of a difference between the product of the voltage ($V_B$) and current ($I_B$) and the first fault power level, based on charging, is less than a power re-pass hysteresis calibration. The minimum pass power threshold, for charging, provides the ability to specify the minimum amount of battery power which must be accepted during a drive cycle to allow the CDM 50 to produce a pass result. The minimum pass power duration provides the ability to choose how many diagnostic executions the minimum passing power must be exceeded in order for the CDM 50 to be allowed to pass. The first fault power level is the instantaneous battery power at the moment the CDM 50 produces a fail result after a pass result. This value may be used in the next pass conditions of the diagnostic. The first fault power initialization calibration provides the ability to specify the initial value for the first fault power value when the power level is reset. The minimum re-pass conditions met duration provides the ability to choose how long a full set of re-pass conditions must be met in order for the CDM 50 to be allowed to pass. The first fault state of charge ($SOC_{FF}$) is the value of the state of charge ($SOC_B$) at the moment the CDM 50 produces a fail result after a pass result. The state of charge re-pass hysteresis calibration ($SOC_{RPC}$) is the ability to choose how close the actual state of charge ($SOC_B$) must be to the first fault state of charge ($SOC_{FF}$) in order to allow the diagnostic to re-pass. The power re-pass hysteresis calibration provides the ability to choose how close the actual battery power must be to the first fault power in order to allow the diagnostic to re-pass.

If the determination is made at step 114 that the pass conditions are not met, the method proceeds to step 116. At step 116, the data manager 49 is alerted that the pass conditions are not met and the method 100 returns to step 101, where the algorithm repeats. If, however, the determination is made at step 114 that the pass conditions are met for the CDM 50, the CDM 50 terminates and the method proceeds to step 118, which will be explained in more detail below.

Similar to the steps described in steps 106-114, as mentioned above, once step 104 is complete, the method also proceeds to step 120, in parallel with step 106. At step 120, a determination is made as to whether the DDM 52 should be enabled. More specifically, the controller 34 determines that the DDM 52 may be enabled when only certain conditions are met. These conditions may include, but should not be limited to, determining that the voltage ($V_B$), state of charge ($SOC_B$), minimum battery temperature ($T_{BMIN}$), maximum battery temperature ($T_{BMAX}$), current ($I_B$), and a calculated discharging power limit are all available and also determining that the ignition signal 40 is being received. The calculated discharging power level provides the ability to choose which of the high voltage battery discharging power limits are observed in the DDM 52. The conditions may also require the voltage ($V_B$), state of charge ($SOC_B$), minimum battery temperature ($T_{BMIN}$), maximum battery temperature ($T_{BMAX}$), current ($I_B$), and the calculated discharging power limit are not fault active at the same time the ignition signal 40 is consecutively being received. Further conditions may include that the state of charge ($SOC_B$) is greater than or equal to a minimum enabled state of charge ($SOC_{EMIN}$), based on a discharging calibration; the state of charge ($SOC_B$) is less than or equal to a maximum enabled state of charge ($SOC_{EMAX}$), based on the discharging calibration; the maximum temperature ($T_{BMAX}$) is less than or equal to a calibrated maximum enabled temperature ($T_{EMAX}$); the minimum temperature ($T_{BMIN}$) is greater than or equal to the calibrated minimum enabled temperature ($T_{EMIN}$); and a difference between the maximum temperature ($T_{BMAX}$) and minimum temperature ($T_{BMIN}$) is less than or equal to the calibrated maximum delta temperature ($T_{\Delta MAX}$). Other conditions may be required in order to enable the DDM 52. The minimum enabled state of charge ($SOC_{EMIN}$) provides the ability to choose the lowest value for the battery state of charge ($SOC_B$), for which the DDM 52 will still be enabled. The maximum enabled state of charge ($SOC_{EMAX}$) provides the ability to choose the highest value for the battery state of charge ($SOC_B$), for which the DDM 52 will still be enabled.

If the determination is made at step 120 that the DDM 52 should not be enabled, the method returns to step 101, where the method 100 is repeated. If, however, the determination is made at step 120 that the DDM 52 should be enabled, the method proceeds to step 122, where the DDM 52 is enabled.

Next, the method proceeds from step 122 to step 124. At step 124 a determination is made as to whether fault conditions are met, based on a discharging calibrated threshold. More specifically, at step 124, fault conditions are met if, based on the discharging calibrated threshold, the calculated discharging power limit indicates lesser power capability than an end of life power threshold, based on the discharging calibrated threshold, for the relevant battery state of charge ($SOC_B$) and the battery minimum temperature ($T_{BMIN}$). The end of life power threshold provides the ability to choose the discharging power threshold for fault for the DDM 52.

If the determination is made at step 124 that the fault conditions are met, the method proceeds to step 126. At step 126, the status of the fault conditions not being met is recorded in a memory location within the data manager 49 and the method 100 returns to step 101, where the algorithm repeats. If, however, the determination is made at step 124 that the fault conditions are not met, the method 100 proceeds to step 128.

At step 128, a determination is made as to whether pass conditions are met for the DDM 52. More specifically, the pass conditions are met if all of the following have occurred while the ignition signal 40 (i.e., RUN/CRANK) was consecutively True: (1) a product of the voltage ($V_B$) and the current ($I_B$) are of greater power in the discharging direction than a minimum pass power threshold, based on the discharging calibration, as a function of the relevant battery state of charge ($SOC_B$) and the minimum battery temperature ($T_{BMIN}$), for greater than a minimum pass power duration, based on a discharging calibrated number of consecutive diagnostic executions; and (2) either of the following occur: (a) a first fault power level, for discharging, is equal to the first fault power initialization calibration; or (b) all of the following are true for greater than a minimum re-pass condition met duration, for discharging, based on a calibrated consecutive number of diagnostic executions: (i) a first fault power level, for discharging, is not equal to the first fault power initialization calibration; (ii) the absolute value of a difference between the battery state of charge ($SOC_B$) and a first fault state of charge ($SOC_{FF}$), for discharging, is less than a re-pass state of charge hysteresis calibration ($SOC_{RPC}$); and (iii) the absolute value of a difference between the product of the voltage ($V_B$) and current ($I_B$) and the first fault power level, based on discharging, is less than a re-pass power hysteresis calibration. The minimum pass power threshold, based on the discharging, provides the ability to specify the minimum amount of battery power which must be accepted during the drive cycle to allow the DDM 52 to produce a pass result. The minimum pass power duration, based on a discharging, provides the ability to choose how many diagnostic executions the minimum passing power must be exceeded in order for the DDM 52 to be allowed to pass. The first fault power level, for discharging, is a stored instantaneous battery power at the moment the DDM 52 produces a fail result after a pass result. This value is used in the next pass conditions of the diagnostic. The minimum re-pass conditions met duration, for discharging, provides the ability to choose how long the full set of re-pass conditions must be met in order for the DDM 52 to be allowed to pass. The first fault state of charge ($SOC_{FF}$), for discharging, is the value of the battery state of charge ($SOC_B$) at the moment the DDM 52 produces a fail result after a pass result.

If the determination is made at step 128 that the pass conditions are not met, the method proceeds to step 129. At step 129, the data manager 49 is alerted that the pass conditions are not met and the method 100 returns to step 101, where the algorithm repeats. If, however, the determination is made at step 128 that the pass conditions are met for the DDM 52, the DDM 52 terminates and the method 100 proceeds to step 118.

At step 118, the results of steps 114 (CDM 50) and 128 (DDM 52) are recorded in a memory location within the data manager 49. The results may be whether the respective module 50, 52 passed or did not pass. Once the results are recorded at step 118, the method then proceeds to step 130.

At step 130, the results are retrieved from the memory location within the data manager 49. Once the results are retrieved at step 130, the method 100 proceeds to step 132.

At step 132, a determination is made as to whether the pass conditions were met for both modules 50, 52; only one of the modules 50, 52; or none of the modules 50, 52. If the pass conditions were met for both modules 50, 52, the method proceeds to step 134, where the indication of the passage by both modules is recorded in a memory location of the data manager 49. After step 132, the method returns to step 101, where the algorithm is repeated.

If the pass conditions were met for only one of the modules 50, 52, the method 100 proceeds to step 136, where the indication of the passage by only one module 50, 52 is recorded in a memory location of the data manager 49.

If the pass conditions were not met for either module, the method 100 proceeds from step 132 to step 138, where the indication that none of the modules 50, 52 passed is recorded in a memory location of the data manager 49.

After steps 136 and/or 138, the method 100 may return to step 101, where the algorithm is repeated. However, alternatively, the steps 136 and/or 138 may proceed to another algorithm that may attempt to duplicate the fault conditions and non-passage of the respective CDM 50 and DDM 52.

While the best modes for carrying out the many aspects of the present teachings have been described in detail, those familiar with the art to which these teachings relate will recognize various alternative aspects for practicing the present teachings that are within the scope of the appended claims.

The invention claimed is:

1. A method for monitoring a performance level of a battery of a vehicle having an electronic control unit (ECU), comprising:

enabling a charging diagnostic module (CDM);

determining, with the CDM, a charging status of the battery;
enabling a discharging diagnostic module (DDM);
determining, with the DDM, a discharging status of the battery; and
recording the charging status and the discharging status in a memory location of the ECU.

2. The method of claim 1, wherein enabling a CDM and enabling a DDM are simultaneous.

3. The method of claim 1, further comprising retrieving values of the battery from a memory location of the ECU.

4. The method of claim 3, wherein enabling a CDM is further defined as enabling a CDM as a function of the values retrieved from the memory location of the ECU meeting predefined conditions; and
wherein enabling a DDM is further defined as enabling a DDM as a function of the values retrieved from the memory location of the ECU meeting predefined conditions.

5. The method of claim 3, wherein the values include at least one of a voltage, a state of charge, a minimum battery temperature, a maximum battery temperature, and a current of the battery.

6. The method of claim 5, wherein the values further include a calculated charging power limit of the battery.

7. The method of claim 3, further comprising determining that an ignition signal is being received by the ECU.

8. The method of claim 3, wherein determining, with the CDM, a charging status of a battery is further defined as determining, with the CDM, a charging status of the battery, as a function of the values retrieved from the memory location of the ECU; and
wherein determining, with the DDM, a discharging status of a battery is further defined as determining, with the DDM, a discharging status of the battery, as a function of the values retrieved from the memory location of the ECU.

9. The method of claim 8, wherein the charging status of the battery is determined to be passing only when pass conditions for the CDM are met;
wherein the charging status of the battery is determined to be not passing only when the pass conditions for the CDM are not met;
wherein the discharging status of the battery is determined to be passing only when pass conditions for the DDM are met; and
wherein the discharging status of the battery is determined to be not passing only when the pass conditions for the DDM are not met.

10. The method of claim 9, further comprising:
retrieving the charging status and the discharging status from the memory location;
determining the performance level of the battery as a function of the retrieved charging status and discharging status;
wherein the performance level is determined to be at a performing level when the retrieved charging status and discharging status are each determined to be passing; and
wherein the performance level is determined to not be at a performing level when the retrieved charging status and discharging status are each determined to not be passing.

11. A vehicle comprising:
a battery; and
an electronic control unit (ECU) including a controller in communication with the battery;
wherein the controller is configured to:
enable a charging diagnostic module (CDM);
determine, with the CDM, a charging status of the battery;
enable a discharging diagnostic module (DDM);
determine, with the DDM, a discharging status of the battery; and
record the charging status and the discharging status in a memory location of the ECU.

12. The vehicle of claim 11, wherein enabling a CDM is simultaneous with enabling a DDM.

13. The vehicle of claim 11, wherein the controller is further configured to retrieve values of the battery from a memory location of the ECU.

14. The vehicle of claim 13, wherein the controller is configured to enable the CDM as a function of the values retrieved from the memory location of the ECU meeting predefined conditions; and
wherein the controller is configured to enable the DDM as a function of the values retrieved from the memory location of the ECU meeting predefined conditions.

15. The vehicle of claim 13, wherein the values include at least one of a voltage, a state of charge, a minimum battery temperature, a maximum battery temperature, and a current of the battery.

16. The vehicle of claim 15, wherein the values further include a calculated charging power limit of the battery.

17. The vehicle of claim 13, further comprising an ignition system configured to transmit an ignition signal to the controller in response to receiving an input;
wherein the controller is further configured to retrieve values from the memory location of the ECU in response to the controller determining that an ignition signal is being received by the ECU.

18. The vehicle of claim 13, wherein the controller is further configured to:
determine the charging status of a battery as a function of the values retrieved from the memory location of the ECU; and
determine the discharging status of the battery as a function of the values retrieved from the memory location of the ECU.

19. The vehicle of claim 18, wherein the controller is further configured to:
determine the charging status of the battery to be passing only when pass conditions for the CDM are met;
determine the charging status of the battery to be not passing only when the pass conditions for the CDM are not met;
determine the discharging status of the battery to be passing only when pass conditions for the DDM are met; and
determine the discharging status of the battery to be not passing only when the pass conditions for the DDM are not met.

20. The vehicle of claim 19, wherein the controller is further configured to:
retrieve the charging status and the discharging status from the memory location;
determine the performance level of the battery as a function of the retrieved charging status and discharging status;
wherein the performance level is determined to be at a performing level when the retrieved charging status and discharging status are each determined to be passing; and wherein the performance level is determined to not be at a performing level when the retrieved charging status and discharging status are each determined to not be passing.

* * * * *